United States Patent
Suter et al.

(10) Patent No.: US 12,119,109 B2
(45) Date of Patent: Oct. 15, 2024

(54) METHOD AND DEVICES FOR TRACKING LABORATORY RESOURCES

(71) Applicant: Roche Diagnostics Operations, Inc., Indianapolis, IN (US)

(72) Inventors: Urs Suter, Zurich (CH); Javier Jimenez Roda, Lucerne (CH); Stefan Bucheli, Grosswangen (CH); Isabella Kanne Castejon, Zurich (CH); Dirk Abeln, Zug (CH)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 560 days.

(21) Appl. No.: 17/207,957

(22) Filed: Mar. 22, 2021

(65) Prior Publication Data
US 2021/0304886 A1 Sep. 30, 2021

(30) Foreign Application Priority Data
Mar. 26, 2020 (EP) ..................................... 20165929

(51) Int. Cl.
*G16H 40/40* (2018.01)
*G03H 1/00* (2006.01)
(Continued)

(52) U.S. Cl.
CPC ........... *G16H 40/40* (2018.01); *G03H 1/0005* (2013.01); *G06F 16/955* (2019.01); *G06T 11/00* (2013.01);
(Continued)

(58) Field of Classification Search
CPC ........ G16H 40/40; G16H 10/40; G16H 40/63; G03H 1/0005; G03H 2210/52;
(Continued)

(56) References Cited

U.S. PATENT DOCUMENTS 9,832,412 B2 11/2017 Burkholz et al.
11,099,057 B2 * 8/2021 Madadin ................ G01G 21/28
(Continued)

FOREIGN PATENT DOCUMENTS

JP 2017-187962 A 10/2017
JP 2019-067415 A 4/2019
(Continued)

OTHER PUBLICATIONS

Anonymous, Augmented reality, Wikipedia, 2020, retrieved from https://en.wikipedia.org/w/index.php?title=Augmented_reality@oldid=947233389, 46 pp.
(Continued)

*Primary Examiner* — Maurice L. McDowell, Jr.
(74) *Attorney, Agent, or Firm* — KATTEN MUCHIN ROSENMAN LLP

(57) ABSTRACT

A computer-implemented method for tracking laboratory resources is disclosed. The laboratory resource comprises an identification feature. The method comprises an identification step comprising detecting the laboratory resource in the laboratory with an imaging sensor of an augmented reality device and identifying the laboratory resource with an identification unit of the augmented reality device by receiving identification information from the identification feature, a data retrieving step comprising retrieving information about the identified laboratory resource from a data server via a communication interface of the augmented reality device, and a tracking step comprising generating and displaying augmented reality information on a display device of the augmented reality device. The augmented reality information comprises a hologram comprising the retrieved information about the identified laboratory resource and/an instruction depending on the retrieved information about the identified laboratory resource.

16 Claims, 4 Drawing Sheets

(51) Int. Cl.
*G06F 16/955* (2019.01)
*G06T 11/00* (2006.01)
*G06V 20/52* (2022.01)
*H04L 67/02* (2022.01)
*H04L 67/12* (2022.01)

(52) U.S. Cl.
CPC .............. *G06V 20/52* (2022.01); *H04L 67/02* (2013.01); *H04L 67/12* (2013.01); *G03H 2210/52* (2013.01); *G03H 2210/53* (2013.01)

(58) Field of Classification Search
CPC ... G03H 2210/53; G06F 16/955; G06F 3/011; G06F 16/21; G06T 11/00; G06T 19/006; G06V 20/52; H04L 67/02; H04L 67/12; G06K 17/0022
See application file for complete search history.

(56) References Cited

U.S. PATENT DOCUMENTS

| | | | | |
|---|---|---|---|---|
| 2010/0007501 A1* | 1/2010 | Yang | ..................... | B01L 3/5453 340/572.8 |
| 2013/0038633 A1* | 2/2013 | Maggiore | ............... | B01L 99/00 29/407.01 |
| 2013/0159135 A1* | 6/2013 | Jones | ..................... | G06Q 10/08 705/26.8 |
| 2017/0142324 A1* | 5/2017 | Jost | ......................... | G16H 40/20 |
| 2018/0247024 A1* | 8/2018 | Divine | .................. | G06T 19/006 |
| 2019/0318659 A1* | 10/2019 | Hamadani | ............... | G06F 3/011 |
| 2019/0362556 A1 | 11/2019 | Ben-dor et al. | | |
| 2021/0090694 A1* | 3/2021 | Colley | ................... | G16H 15/00 |
| 2022/0139046 A1* | 5/2022 | Gantzer | .................. | G06T 13/20 345/419 |

FOREIGN PATENT DOCUMENTS

| | | | | |
|---|---|---|---|---|
| WO | 2013/170204 A1 | 11/2013 | | |
| WO | 2017/033537 A1 | 3/2017 | | |
| WO | 2017/053462 A1 | 3/2017 | | |
| WO | WO-2017199244 A1 * | 11/2017 | ............. | A61D 19/00 |
| WO | WO-2020163218 A1 * | 8/2020 | ............. | G06T 13/20 |

OTHER PUBLICATIONS

European Search Report issued Sep. 11, 2020, in Application No. EP 20165929.9, 2 pp.

Gama, Kiev et al., Combining heterogeneous service technologies for building an Internet of Things middleware, Computer Communications, 2012, pp. 405-417, vol. 35.

* cited by examiner

METHOD AND DEVICES FOR TRACKING LABORATORY RESOURCES

CROSS-REFERENCE TO RELATED APPLICATIONS

This application claims priority to EP 20165929.9, filed Mar. 26, 2020, which is hereby incorporated by reference.

BACKGROUND

The present disclosure generally relates to a computer implemented method and a tracking system for tracking laboratory resources to be used by laboratory staff to support and facilitate workflows.

Laboratory operators need to track in their daily business a state of a large number of different resources. Examples for these resources are sample tubes, instruments, reagent cassettes, processing plates or internal controls. The resources may have their own identity and need to be tracked and managed independently. The resources may be marked with a barcode, which may allow to uniquely identify them.

In known identification methods, the barcode is manually scanned and the information on it is received. This implies that if the operator wants to get the information of a certain resource, such as of one of a reagent cassette placed in a laboratory instrument, the operator needs to directly go to the laboratory instrument and scan the barcode of the reagent cassette there to get the information. Sample tubes may be even more difficult, since potentially only a laboratory information system (LIS) or middleware knows what is the current state of the sample, e.g., what is the sample type, what was the last executed test on it, and its result or what is the next target instrument. To get any of this information, the operator needs to go to a dedicated station, such as of a personal computer or laptop, scan the sample tube barcode and get the information.

It is known in the art to include the usage of a tablet device or smartphones to get this information from the different resources. However, since this approach does not include aggregating the underlying laboratory data the need for different applications for different systems is not resolved. Moreover, the operation of such devices itself still remains difficult in a laboratory environment in which the operator usually needs to wear protection gloves impeding the application of touchable screens and in which the operator furthermore often coercively needs both hands during workflows: one to handle the resource and the other to handle the tablet or smartphone. Besides the difficulties with the operation of such touchable screens in a laboratory environment, also screen size, which can be too small for some operators in some situations, remains a problem. Finally, in order to operate with the different instruments of the laboratory, the operator needs to physically be in front of each instrument.

Therefore, there is a need for a computer implemented method and a tracking system for tracking of at least one laboratory resource in a laboratory which at least partially avoid the shortcomings of known devices and methods of this kind and allow simplified and, for an operator, comfortable identification of laboratory resources.

SUMMARY

According to the present disclosure, a computer-implemented method for tracking of at least one laboratory resource in a laboratory is presented. The laboratory resource can comprise at least one identification feature. The method can comprising at least one identification step, detecting the laboratory resource in the laboratory with at least one imaging sensor of at least one augmented reality device and identifying the laboratory resource with at least one identification unit of the augmented reality device by receiving at least one identification information from the identification feature; at least one data retrieving step comprising retrieving information about the identified laboratory resource from at least one data server via at least one communication interface of the augmented reality device, at least one tracking step comprising generating and displaying at least one augmented reality information on at least one display device of the augmented reality device, wherein the augmented reality information comprises at least one hologram comprising the retrieved information about the identified laboratory resource and/or at least one instruction depending on the retrieved information about the identified laboratory resource; and at least one data publishing step comprising at least one Laboratory Information System (LIS) and/or middleware and/or instrument of the laboratory publishing data about the laboratory resource and/or the laboratory and/or the instrument on the data server.

Accordingly, it is a feature of the embodiments of the present disclosure to provide a computer implemented method and a tracking system for tracking of at least one laboratory resource in a laboratory which at least partially avoid the shortcomings of known devices and methods of this kind and allow simplified and, for an operator, comfortable identification of laboratory resources. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
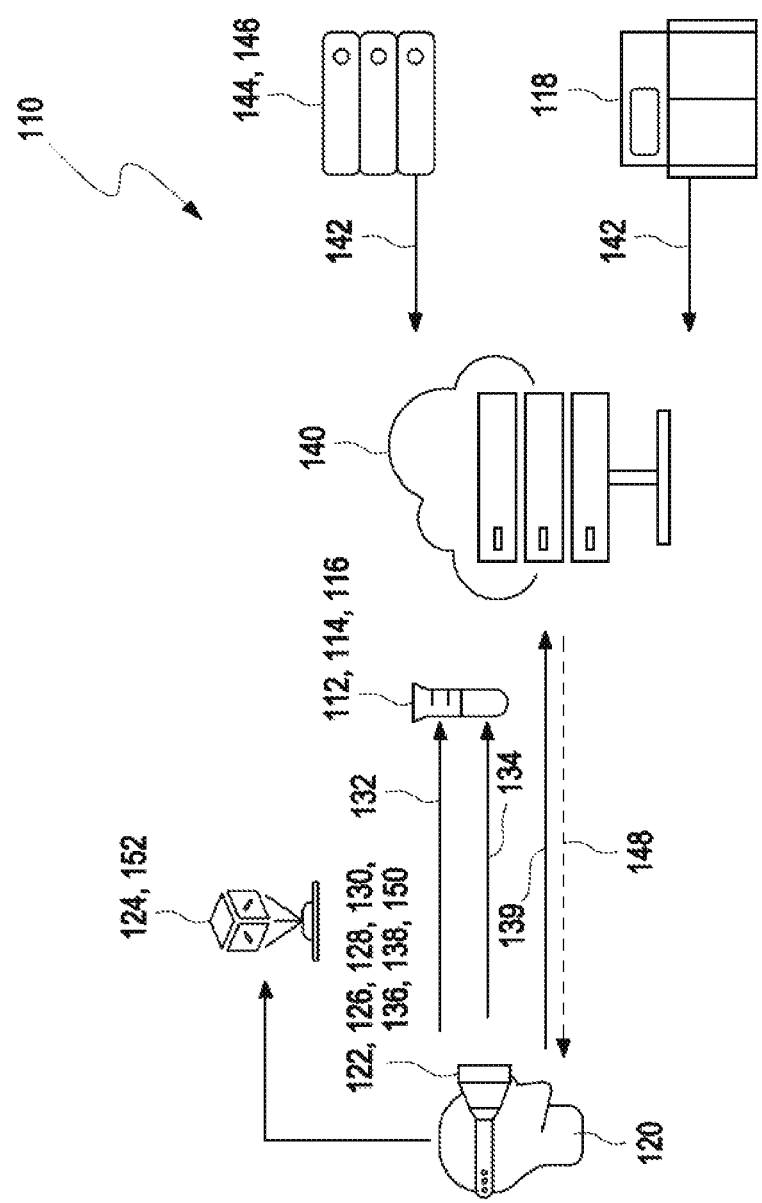
FIG. 1 illustrates a tracking system and a method for tracking at least one laboratory resource used for tracking a sample tube in a laboratory according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used in the following, the terms "have", "comprise" or "include" or any arbitrary grammatical variations thereof can be used in a non-exclusive way. Thus, these terms may both refer to a situation in which, besides the feature introduced by these terms, no further features can be present in the entity described in this context and to a situation in which one or more further features can be present. As an example, the expressions "A has B", "A comprises B" and "A includes B" may both refer to a situation in which, besides B, no other element may be present in A (i.e. a situation in which A solely and exclusively can consist of B) and to a situation in which, besides B, one or more further elements can be present in entity A, such as element C, elements C and D or even further elements.

Further, it can be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" may not be repeated, non-withstanding the fact that the respective feature or element may be present once or more than once.

Further, as used in the following, the terms, "particularly", "more particularly", "specifically", "more specifically" or similar terms can be used in conjunction with optional features, without restricting alternative possibilities. Thus, features introduced by these terms can be optional features and may not be intended to restrict the scope of the claims in any way. The present disclosure may, as the skilled person will recognize, be performed by using alternative features. Similarly, features introduced by "in an embodiment of the present disclosure" or similar expressions can be intended to be optional features, without any restriction regarding alternative embodiments of the present disclosure, without any restrictions regarding the scope of the invention and without any restriction regarding the possibility of combining the features introduced in such way with other optional or non-optional features of the present disclosure.

In a first aspect of the present disclosure, a computer-implemented method for tracking of at least one laboratory resource in a laboratory is disclosed.

The term "computer implemented method" as used herein can be a broad term and can be given its ordinary and customary meaning to a person of ordinary skill in the art and may not be limited to a special or customized meaning. The term specifically may refer, without limitation, to a method involving at least one computer and/or at least one computer network. The computer and/or computer network may comprise at least one processor, which can be configured for performing at least one of the method steps of the method according to the present disclosure. Specifically, each of the method steps can be performed by the computer and/or computer network. The method may be performed completely automatically, specifically without user interaction. The term "automatically" as used herein can be a broad term and can be given its ordinary and customary meaning to a person of ordinary skill in the art and may not be limited to a special or customized meaning. The term specifically may refer, without limitation, to a process, which can be performed completely by at least one computer and/or computer network and/or machine, in particular without manual action and/or interaction with a user.

The term "laboratory" as used herein can be a broad term and can be given its ordinary and customary meaning to a person of ordinary skill in the art and may not be limited to a special or customized meaning. The term specifically may refer, without limitation, to at least one environment comprising at least one analyzer and/or at least one instrument configured for analyzing at least one sample. The laboratory may be a location configured for work in the field of the natural sciences and/or engineering in the sense that it can offer the opportunity to conduct corresponding measurements and controls.

The term "laboratory resource" as used herein can be a broad term and may be given its ordinary and customary meaning to a person of ordinary skill in the art and may not be limited to a special or customized meaning. The term specifically may refer, without limitation, to any physical object and/or information present in the laboratory. The laboratory resource may comprise at least one element selected from the group consisting of: at least one sample tube; at least one reagent cassette; at least one processing plate; at least one instrument; at least one internal control and the like. The term "instrument" as used herein can be a broad term and can be given its ordinary and customary meaning to a person of ordinary skill in the art and may not be limited to a special or customized meaning. The term specifically may refer, without limitation, to an arbitrary device configured for analyzing at least one sample. For example, the instrument may be configured for conducting at least one chemical analysis. The term "internal control" as used herein can be a broad term and can be given its ordinary and customary meaning to a person of ordinary skill in the art and may not be limited to a special or customized meaning. The term specifically may refer, without limitation, to at least one element of a control mechanism using at least one control material, in particular a control sample, configured for one or more of detecting, reducing and correcting deficiencies in an analysis process of the laboratory.

The term "tracking" as used herein can be a broad term and can be given its ordinary and customary meaning to a person of ordinary skill in the art and may not be limited to a special or customized meaning. The term specifically may refer, without limitation, to a process of determining position and/or status of at least one laboratory resource at at least one time point, specifically at at least two different time points. For example, the tracking may comprise determining position and/or status of at least one laboratory resource at an arbitrary time point.

The laboratory resource can comprise at least one identification feature. The term "identification feature" as used herein can be a broad term and can be given its ordinary and customary meaning to a person of ordinary skill in the art and may not be limited to a special or customized meaning. The term specifically may refer, without limitation, to an arbitrary feature suitable for identification of the laboratory resource. The identification feature may be or comprise any aspect, character or detail of the laboratory resource. The identification feature may, for example, be or may comprise one or more of shape, color or identification tags placed on it. The identification feature may be configured for visually distinguishing the laboratory resource from other laboratory resources. The identification feature may comprise at least one element or a combination of elements configured for storing one or more items of information identifying the laboratory resource, such as in a readable fashion, specifically in a machine-readable fashion. The identification feature may comprise at least one of an optical identification feature, an electronic identification feature, a magnetic identification feature or a mechanical identification feature. The identification feature may comprise at least one marker. As an example, the identification feature, specifically the optical identification feature, may be or may comprise at least one of a one- or two-dimensional code and/or a readable information tag, such as one or more of a barcode, a QR code or another type of code directly or indirectly attached to the laboratory resource, such as by being applied directly to the laboratory resource and/or by being attached to the laboratory resource via at least one label or tag. The information stored in the identification feature may be read using an appropriate reading device. The identification feature may comprise one or more of at least one barcode, at least one QR code, at least one radio frequency identification tag, and at least one near field communication tag.

The identification feature may comprise identification information. The term "identification information" as used herein can be a broad term and can be given its ordinary and customary meaning to a person of ordinary skill in the art and may not be limited to a special or customized meaning. The term specifically may refer, without limitation, to information configured for identifying the laboratory resource and/or a status of the laboratory resource. As an example, the identification information specifically may comprise at least one identification number of the laboratory resource. The identification information may comprise one or more of shape, color, barcode, RFID tag, or other tagging systems. The term "identification number" as used herein can be a broad term and can be given its ordinary and customary meaning to a person of ordinary skill in the art and may not be limited to a special or customized meaning. The term specifically may refer, without limitation, to one or more of an array or a sequence of numbers and/or letters encoding the identification information of a specific laboratory resource. The identification number may be unique for a specific laboratory resource. Thus, it may be possible to identify a specific laboratory resource according to the respective identification number.

The term "barcode" as used herein can be a broad term and can be given its ordinary and customary meaning to a person of ordinary skill in the art and may not be limited to a special or customized meaning. The term specifically may refer, without limitation, to binary optical information, such as to a binary sequence of optical information, such as a sequence of parallel lines having different widths, the binary sequence encoding information such as a number and/or an array of numbers and/or letters. Thus, the barcode may be a sequence of single colored lines having a high contrast compared to a background. Specifically, the barcode may comprise black lines on a white background.

The term "QR code" as used herein can be a broad term and can be given its ordinary and customary meaning to a person of ordinary skill in the art and may not be limited to a special or customized meaning. The term specifically may refer, without limitation, to a quadratic matrix of binary pixels, the matrix encoding information such as a number and/or an array of numbers and/or letters. The pixels of the quadratic matrix may have a high contrast compared to a background. Specifically, the pixels of the matrix may comprise black squares arranged on a white background. Further, the QR code may comprise an indication of orientation enabling a reading device of the QR code to align the matrix.

The term "RFID tag" as used herein can be a broad term and can be given its ordinary and customary meaning to a person of ordinary skill in the art and may not be limited to a special or customized meaning. The term specifically may refer, without limitation, to a label configured for exchanging data information with a reading device by using radio-frequency electromagnetic radiation, in particular by using the NFC standard. The RFID tag may further comprise an antenna configured to receive and to emit a radio-frequency signal and an electronic chip such as a microchip configured to store the data information. Specifically, the RFID tag may be a flexible substrate having an electronic conducting coil and optionally at least one microchip.

The method can comprise the following steps, which, as an example, may be performed in the given order. It can be noted, however, that a different order may also be possible. Further, it can also be possible to perform one or more of the method steps once or repeatedly. Further, it can be possible to perform two or more of the method steps simultaneously or in a timely overlapping fashion. The method may comprise further method steps, which are not listed.

The method can comprise:
a) at least one identification step, wherein the identification step can comprise detecting the laboratory resource in the laboratory with at least one imaging sensor of at least one augmented reality device and identifying the laboratory resource with at least one identification unit of the augmented reality device by receiving at least one identification information from the identification feature;
b) at least one data retrieving step, wherein the data retrieving step can comprise retrieving information about the identified laboratory resource from at least one data server via at least one communication interface of the augmented reality device; and
c) at least one tracking step, wherein the tracking step can comprise generating and displaying at least one augmented reality information on at least one display device of the augmented reality device, wherein the augmented reality information can comprise at least one hologram comprising the retrieved information about the identified laboratory resource and/or at least one instruction depending on the retrieved information about the identified laboratory resource.

Steps a) to c) may be performed fully automatically. The term "fully automatically" as used herein can be a broad term and can be given its ordinary and customary meaning to a person of ordinary skill in the art and may not be limited to a special or customized meaning. The term specifically may refer, without limitation; to that steps a) to c) involve using at least one computer and/or at least one computer network. Specifically, steps a) to c) may be performed without the laboratory operator taking any action during identification of the laboratory resource other than looking at it through the augmented reality device. The laboratory operator may not need to be in any specific location. Specifically, the data server involved in the retrieving step b) may comprise one or more of at least one computer, at least one computer network, and at least one cloud server.

The term "augmented reality device" as used herein can be a broad term and can be given its ordinary and customary meaning to a person of ordinary skill in the art and may not be limited to a special or customized meaning. The term specifically may refer, without limitation, to an arbitrary device, which can be configured for augmenting an image of a physical object with computer-based additional information. The additional information may be denoted as augmented reality information in the following. The augmented reality information may comprise, for example, visual and/or auditory information. The augmented reality information may be at least one virtual object from a data server by picture-in-picture fade-in. The augmented reality information may be constructive such as an additive or may be destructive such as by masking. The augmented reality device may comprise one or more of at least one processing device, at least one display device, at least one sensor, such as the at least one imaging sensor, at least one accelerometer, at least one gyroscope and the like, and at least one input device. The augmented reality device may comprise an optical projection system configured for projecting augmented reality information to a laboratory operator.

The augmented reality device may be at least one portable and/or wearable augmented reality device. The augmented reality device as a whole may further be portable and/or wearable, so that it may easily be positioned in the laboratory at a position of interest. The augmented reality device may be worn by the user such as by a laboratory operator. The augmented reality device may comprise eyeglasses. For example, the augmented reality device may be designed as Microsoft HOLOLENS™ device.

The term "imaging sensor" as used herein can be a broad term and can be given its ordinary and customary meaning to a person of ordinary skill in the art and may not be limited to a special or customized meaning. The term specifically may refer, without limitation, to at least one sensor device having at least one imaging element configured for recording or capturing spatially resolved one-dimensional, two-dimensional or even three-dimensional optical data or information. As an example, the imaging sensor may comprise at least one camera chip, such as at least one CCD chip and/or at least one CMOS chip configured for recording images. The imaging sensor may be configured for generating and/or recording at least one image of the laboratory resource and/or at least one part of the laboratory resource, such as of the identification feature. The imaging sensor may be integrated in the augmented reality device. As further used herein, the term "detecting the laboratory resource" can be a broad term and can be given its ordinary and customary meaning to a person of ordinary skill in the art and may not be limited to a special or customized meaning. The term specifically may refer, without limitation, to imaging the laboratory resource and/or at least sectors or parts of the laboratory resource. Specifically, the detecting of the laboratory resource may comprise detection of at least one physical object such as sample tube, reagent cassette, instruments and the like, on the physical world.

The term "image" as used herein can be a broad term and can be given its ordinary and customary meaning to a person of ordinary skill in the art and may not be limited to a special or customized meaning. The term specifically may refer, without limitation, to data recorded by using the imaging sensor, such as a plurality of electronic readings from the imaging sensor, such as the pixels of a camera chip. Thus, the image may be or may comprise at least one array of information values, such as an array of grey scale values and/or color information values. The image may be a single color image or a multi-color or colored image.

Step a) may comprise imaging the laboratory resource with the imaging sensor and evaluating at least one image of the laboratory resource using at least one processing device of the augmented reality device. Thus, as an example, the augmented reality device may comprise one or more programmable devices such as one or more computers, microprocessors, application-specific integrated circuits (ASICs), Digital Signal Processors (DSPs), or Field Programmable Gate Arrays (FPGAs) which can be configured to perform the evaluation. The evaluation may comprise using at least one image-processing algorithm.

The augmented reality device may comprise the at least one processing device, also denoted processor. The term "processor" as generally used herein can be a broad term and can be given its ordinary and customary meaning to a person of ordinary skill in the art and may not be limited to a special or customized meaning. The term specifically may refer, without limitation, to an arbitrary logic circuitry configured for performing basic operations of a computer or system, and/or, generally, to a device which can be configured for performing calculations or logic operations. In particular, the processor may be configured for processing basic instructions that drive the computer or system. As an example, the processor may comprise at least one arithmetic logic unit (ALU), at least one floating-point unit (FPU), such as a math co-processor or a numeric coprocessor, a plurality of registers, specifically registers configured for supplying operands to the ALU and storing results of operations, and a memory, such as an L1 and L2 cache memory. In particular, the processor may be a multi-core processor. Specifically, the processor may be or may comprise a central processing unit (CPU). Additionally, or alternatively, the processor may be or may comprise a microprocessor, thus specifically the processor's elements may be contained in one single integrated circuitry (IC) chip. Additionally, or alternatively, the processor may be or may comprise one or more application-specific integrated circuits (ASICs) and/or one or more field-programmable gate arrays (FPGAs) or the like. The processor specifically may be configured, such as by software programming, for performing one or more evaluation operations.

The method may comprise positioning the augmented reality device in the laboratory at a position of interest. The laboratory may comprise a plurality of laboratory resources. In the case, the augmented reality device comprises eyeglasses, the laboratory operator may direct the augmented reality device to one of the laboratory resources of interest by looking at it.

Step a) may comprise scanning the identification feature. The term "scanning", also denoted as reading, as used herein can be a broad term and can be given its ordinary and customary meaning to a person of ordinary skill in the art and may not be limited to a special or customized meaning. The term specifically may refer, without limitation, to the process of retrieving at least one item of information, such as the at least one item of information stored in the identification information, such as in an electronic format. The reading specifically may take place electronically. The process of scanning may depend on the type of identification information. Thus, the scanning may comprise an optical reading, in the case, the identification information can comprise an optical identification information, such as a bar code and/or a QR code, e.g., by optical scanning. In the case, the identification information can comprise an electronic identification information, such as an RFID code, the reading may comprise an electronic reading, such as a reading by near field communication (NFC). Other options can be feasible.

The augmented reality device can comprise the at least one identification unit. The term "identification unit" as used herein can be a broad term and can be given its ordinary and customary meaning to a person of ordinary skill in the art and may not be limited to a special or customized meaning. The term specifically may refer, without limitation, to an element of the augmented reality device or designed as a separate device configured for assigning an identity to the imaged laboratory device. The identification unit may comprise at least one reading device. The term "reading device"

as used herein can be a broad term and can be given its ordinary and customary meaning to a person of ordinary skill in the art and may not be limited to a special or customized meaning. The term specifically may refer, without limitation, to a device configured to perform the scanning process as defined above, such as to a device configured to read the identification information stored by the identification feature. Specifically, the reading device may be or may comprise at least one of: a one- or two-dimensional scanner, a camera and/or a radio frequency reading device, such as a NFC reader. The reading device may be integrated into the augmented reality device. Additionally, or alternatively, the reading device may be designed as separate element. The reading device may further be configured to communicate with the identification unit. Specifically, the reading device may be configured to transfer the identification information to the identification unit, such as to a processor of the identification unit. The term "identifying" as used herein can be a broad term and can be given its ordinary and customary meaning to a person of ordinary skill in the art and may not be limited to a special or customized meaning. The term specifically may refer, without limitation, to assigning at least one identity to the imaged laboratory resource.

The term "communication interface" as used herein can be a broad term and can be given its ordinary and customary meaning to a person of ordinary skill in the art and may not be limited to a special or customized meaning. The term specifically may refer, without limitation, to an item or element forming a boundary configured for transferring information. In particular, the communication interface may be configured for transferring information from a computational device, e.g., a computer, such as to send or output information, e.g., onto another device. Additionally, or alternatively, the communication interface may be configured for transferring information onto a computational device, e.g., onto a computer, such as to receive information. The communication interface may specifically provide for transferring or exchanging information. In particular, the communication interface may provide a data transfer connection, e.g., Bluetooth, NFC, inductive coupling or the like. As an example, the communication interface may be or may comprise at least one port comprising one or more of a network or internet port, a USB-port and a disk drive. The communication interface may be at least one web interface.

The term "retrieving information" as used herein can be a broad term and can be given its ordinary and customary meaning to a person of ordinary skill in the art and may not be limited to a special or customized meaning. The term specifically may refer, without limitation, to receiving data and/or downloading data from the data server. Specifically, in step b), the communication interface may transmit at least one request to the data server asking for the information about the identified laboratory resource with the identification information. The request may be a HTTP-based request and/or an AMQP-based request.

The data server may comprise one or more of at least one computer, at least one computer network, at least one cloud server. The data server may be deployed both locally, e.g., on premises, or in the cloud. The data server may comprise at least one database. The term "database" as used herein can be a broad term and can be given its ordinary and customary meaning to a person of ordinary skill in the art and may not be limited to a special or customized meaning. The term specifically may refer, without limitation, to an organized collection of data, generally stored and accessed electronically from a computer or computer system. The database may comprise or may be comprised by a data storage device. The database may comprise at least one data base management system comprising a software running on a computer or computer system, the software allowing for interaction with one or more of a user, an application or the database itself, such as in order to capture and analyze the data contained in the database. The database management system may further encompass facilities to administer the database. The database, containing the data, may, thus, be comprised by a data base system, which, besides the data, can comprise one or more associated applications.

The data server may be configured for subscribing to some events generated by at least one laboratory instrument. The method may comprise at least one data-publishing step. The data server may provide an instance of a Message bus, where instruments of the laboratory and also Laboratory Information System (LIS) and/or middleware can publish information in the shape of events. The data-publishing step may comprise at least one LIS and/or middleware and/or instrument of the laboratory publishing data about the laboratory resource and/or the laboratory and/or the instrument on the data server. The data server may subscribe to those events and use them to project data into the database, such as to a document database, which can be used to return the data to the augmented reality device, when it queries for data. The data server may be configured for generating and storing projected data out of the received events in the database. The term "data publishing step" as used herein van be a broad term and can be given its ordinary and customary meaning to a person of ordinary skill in the art and may not be limited to a special or customized meaning. The term specifically may refer, without limitation, to the process of providing information and/or to allow access to information and/or to make information available for further devices such as for the data servers. Specifically, the data-publishing step may comprise confirming a search request for the laboratory resource of interest filed on the data server together with follow-up actions.

The term "event" as used herein can be a broad term and can be given its ordinary and customary meaning to a person of ordinary skill in the art and may not be limited to a special or customized meaning. The term specifically may refer, without limitation, to a human-machine interaction such as a key press and/or sensor output such as a certain visual signal and/or software commands from other programs. These events may cause a program to execute specific corresponding routines instead of linearly running through the underlying program code.

The term "Laboratory Information System (LIS)" as used herein can be a broad term and can be given its ordinary and customary meaning to a person of ordinary skill in the art and may not be limited to a special or customized meaning. The term specifically may refer, without limitation, to a software tool supporting laboratory workflows and data tracking providing an interface for data exchange with further systems.

The term "middleware" as used herein can be a broad term and can be given its ordinary and customary meaning to a person of ordinary skill in the art and may not be limited to a special or customized meaning. The term specifically may refer, without limitation, to a computer software that can provide a platform and an interface for the communication between different application programs above the level of the operating system of the computer.

The term "message bus" as used herein can be a broad term and can be given its ordinary and customary meaning to a person of ordinary skill in the art and may not be limited to a special or customized meaning. The term specifically may refer, without limitation, to a software infrastructure that can allow different systems, also and specifically cross-computer, to communicate with each other through a shared set of interfaces via message transfer. These messages may for instance and without limitation be data packages, signals or function calls.

The data server may be configured for providing an instance, where instruments and/or the LIS and/or middleware may be given the opportunity to publish information in the shape of events. For this purpose, the message bus may be used. The data server may comprise at least one interface for data access, in particular, at least one HTTP-based interface. Specifically, the data server may provide a RESTFul API, which may enable the augmented reality device to query for data. The RESTful API refers to an Application Programming Interface (API) for the Representational State Transfer (REST) programming paradigm mainly used for web services.

As outlined above, the data server may be configured for subscribing to events, so that a defined routine corresponding to a specific event can be executed. The data server may be configured for projecting data into the database, which may be used to return the data to the augmented reality device, when it queries for data. Besides real time tracking, the data collected by the data server may also later be used for data analytics if needed.

The augmented reality device may be connected to the data server. Retrieving and displaying information and instructions for the identified laboratory resource may be completely performed by the augmented reality device in connection with the data server and do not require any action from the laboratory operator at all. The augmented reality device may directly display augmented reality information on the laboratory resource of interest besides interactive guidance for further action on the user side.

The term "information about the identified laboratory resource" as used herein can be a broad term and can be given its ordinary and customary meaning to a person of ordinary skill in the art and may not be limited to a special or customized meaning. The term specifically may refer, without limitation, to any arbitrary information with respect to the laboratory resource. The information about the identified laboratory resource may comprise at least one information selected from the group consisting of: the identification feature, a lot number, a barcode, a sample type, a tube type, a last available result, a last performed test or protocol, a next target instrument, a next test to be performed, expiration date, time range out of fridge, validity, volume left in compartment, on board time, remaining ticks, instrument state, currently processing test or batch, currently processing order ID, loaded resource status, related resources, next maintenance, software version, allowed test to be run on the instrument, last teaching, schedule of runs, previous results, ordering information, state of loaded samples in the instrument, state of loaded resources in the instrument, status of executing runs, list of pending runs, estimated times till next result and next run start.

The augmented reality device furthermore can comprise a display device. The term "display device" as used herein can be a broad term and can be given its ordinary and customary meaning to a person of ordinary skill in the art and may not be limited to a special or customized meaning. The term specifically may refer, without limitation, to an arbitrary device configured for receiving at least one electrical signal and providing a corresponding visual output. The display device may comprise at least one projector and/or at least one screen. The augmented reality device may comprise at least one head-mounted display (HMD). The display device may be configured for imaging of both the physical world, the real laboratory resource, and virtual objects over the user's field of view.

The augmented reality information can comprise the at least one hologram comprising the retrieved information about the identified laboratory resource and/or at least one instruction depending on the retrieved information about the identified laboratory resource. The term "augmented reality information" as used herein can be a broad term and can be given its ordinary and customary meaning to a person of ordinary skill in the art and may not be limited to a special or customized meaning. The term specifically may refer, without limitation, to a computer-based information about the identified laboratory resource retrieved by the augmented reality device from the data server. This information may comprise, for example, visual and/or auditory information. The augmented reality information may be at least one virtual object from a database. The augmented reality information may be constructive such as an additive or may be destructive such as by masking. The augmented reality information may be or may comprise at least one augmented reality representation of different states of the laboratory resources. The augmented reality information may be or may comprise digital information.

The term "hologram" as used herein can be a broad term and can be given its ordinary and customary meaning to a person of ordinary skill in the art and may not be limited to a special or customized meaning. The term specifically may refer, without limitation, to computer-based content comprising information about the identified laboratory resource. The information about the identified laboratory resource, as outlined above, may be retrieved by the augmented reality device from the data server and may be displayed to the laboratory operator by the display device of the augmented reality device, e.g., via picture-in-picture fade-in.

The hologram may comprise at least one virtual object. The hologram may comprise at least one object selected from the group comprising of: the identification feature, a lot number, a barcode, sample type, tube type, last available result, last performed test or protocol, next target instrument, next test to be performed, expiration date, storage information, validity information, volume information for compartments, on board time, remaining ticks, status information, processing information, loaded resource status, related resources, maintenance information, software version, usage information, last teaching, at least one request, at least one managing or controlling information, at least one handling information, and at least one teaching information, at least one guidance information. The hologram may comprise an underlying interference pattern, which may be generated from superposition of coherent light waves or may be algorithmically calculated. The generation or rendering of the hologram may be very dependent on the used technology. Basically, it may be a combination of geolocation algorithms together with a tagging system. With the tag, the augmented reality device may be able to identify and remember the position of a concrete resource in the laboratory. Specifically, it can remember many resources at the same time. The augmented reality device may keep track of the current position of the augmented reality device itself. With these two pieces of data, i.e., the current geolocation of the augmented reality device and the geolocation of the resource, the system may be able to render the hologram in the correct position.

The augmented reality information can comprise at least one hologram comprising at least one instruction depending on the retrieved information about the identified laboratory resource. The term "instruction depending on the retrieved information about the identified laboratory resource" as used herein can be a broad term and can be given its ordinary and customary meaning to a person of ordinary skill in the art and may not be limited to a special or customized meaning. The term specifically may refer, without limitation, to written instructions and/or commands and/or other visual instructions such as illustrations, images, videos and the like. The instruction may comprise instructions for a laboratory operator of the laboratory and/or instructions for at least one device of the laboratory. The instructions may comprise one or more of at least one request, at least one managing or controlling information, at least one handling information, and at least one teaching information. The term "operator" may refer to a user of the augmented reality device and or any of the systems in the laboratory.

The method may comprise the augmented reality device associating the hologram and the laboratory resource such that the hologram can be displayed next to the laboratory resource on the display device. The term "associating" as used herein can be a broad term and can be given its ordinary and customary meaning to a person of ordinary skill in the art and may not be limited to a special or customized meaning. The term specifically may refer, without limitation, to relating and/or combining the laboratory resource and the hologram. Specifically, the associating may comprise generating an indication to which laboratory resource the hologram refers to. The term "next to the laboratory resource on the display device" as used herein can be a broad term and can be given its ordinary and customary meaning to a person of ordinary skill in the art and may not be limited to a special or customized meaning. The term specifically may refer, without limitation, to the fact that the location of the hologram and the laboratory resource can be displayed in direct vicinity, wherein deviations from a direct vicinity can be possible, and/or to the presence of an indication pointing from the hologram to the laboratory resource on the display device. The augmented reality device may be configured for rendering of a hologram next to the physical object. As outlined above, the generation or rendering of the hologram may be performed by combination of geolocation algorithms, tracking and tagging. The distance between the laboratory resources and the hologram may be something that can be configured but no more than about 50 cm of distance can be recommended. The term "on the display device" may comprise embodiments wherein the hologram can be displayed on a screen of the display device and embodiments wherein the display device can comprise the at least one projector projecting the hologram.

For example, the laboratory resource may comprise the sample tube. The hologram may comprise one or more of a barcode, a sample type, a tube type, information about a test result, and information about a test such as a test protocol. The term "test" as used herein can be a broad term and can be given its ordinary and customary meaning to a person of ordinary skill in the art and may not be limited to a special or customized meaning. The term specifically may refer, without limitation, to experiments such as at least one chemical analysis involving the sample tube. As the described method, these experiments also follow certain sequences of steps filed in test protocols. They further can already be completed in the past with corresponding test results. In this example, the laboratory operator wearing the augmented reality device may directly look at the sample tube of interest. The augmented reality device may then first identify the laboratory resource the laboratory operator is looking at, such as by detecting a shape or information tag. Once it is identified that the laboratory resource is a sample tube, the augmented reality device may start scanning for the identification tag. Once the identification tag is read, the augmented reality device may send a HTTP-based request to the data server asking for information on the the sample tube. The data server may then return the requested information, if available, or "nothing" in the case the sample tube is not known. The information "nothing" may comprise information that the identification information is not known or present in the database and/or a prompt to repeat step a) and/or to update the database. With this, the augmented reality device may render a hologram next to the laboratory resource showing the received information including for instance the information feature, the sample type, the tube type, the corresponding last available result, performed test or protocol, the next target instrument or the next test to be performed. Repeating the operation may be possible at any time by looking at the sample tube again.

For example, the laboratory resource may comprise the reagent cassette. The hologram may comprise one or more of a lot number, a barcode, expiration date, storage information, validity information, and status information. Reagent Cassettes may be special, because they may be stored in a refrigerator and may stay out of the refrigerator only for a certain amount of time without changing properties. Therefore, it may be important to track, how long a reagent cassette has been out of the refrigerator. Furthermore, an instrument may invalidate a reagent cassette due to multiple reasons and the laboratory operator may need to know if a reagent cassette is still valid or not, before loading it into an instrument. Finally, a reagent cassette may be made out of one or more compartments, which may contain different liquids. Some instruments may use all compartments, others only a few. It may be of importance for the laboratory operator to know, how much volume is left on each compartment in order to distinguish, whether this reagent cassette may be adequate for a specific test or not. In this example, the laboratory operator wearing the augmented reality device may again directly look at the reagent cassette of interest. The augmented reality device may then first identify the laboratory resource the laboratory operator is looking at, such as by detecting a shape or information tag. Once it is detected that the laboratory resource is a reagent cassette, the augmented reality device may start scanning for the identification tag. Once the identification tag is read, the application may send a HTTP-based request to the data server asking for information on the reagent cassette. The server may then return the requested information, if available, or "nothing" in the case the reagent cassette is not known. With this, the augmented reality device may render a hologram next to the laboratory resource showing the received information including for instance the lot number, the barcode, the expiration date, how long the reagent cassette has been out of the refrigerator, if it is valid or invalid, how much volume is left on each compartment, the on board time if the reagent cassette is inside an instrument or the remaining ticks, e.g., uses. As before, repeating the operation may be possible at any time by looking at the reagent cassette again.

For example, the laboratory resource may comprise at least one instrument. The hologram may comprise one or more of status information, processing information, maintenance information, software version, a list of related resources, and usage information. The instrument may not comprise an intrinsic display device. The instrument may be operated through an application deployed on a separate personal computer (PC) or laptop. This may result in that the laboratory operator may move to another location in order to interact with the instrument like during a simple status control. The laboratory operator wearing the augmented reality device may directly look at the instrument of interest. The augmented reality device may then identify the laboratory resource the laboratory operator is looking at by detecting a shape or a marker. For instruments, a marker may be used to identify the kind of instrument the laboratory operator is looking at. Once it is detected that the laboratory resource is an instrument, the augmented reality device may start scanning for a serial number. Once the serial number is read, the augmented reality device may send a HTTP-based request to the data server asking for information on the instrument. The server may then return the requested information, if available, or "nothing" in the case the instrument is not known. With this, the augmented reality device may render the hologram next to the laboratory resource in the display device showing the received information including for instance the instrument status, the currently processing test, batch or order ID, the status of the loaded resource, the next scheduled maintenance, the running software version, the allowed tests to be run on it or the last teaching. Repeating the operation may be possible at any time by looking at instrument again.

As mentioned above, besides information on the laboratory resource the augmented reality information may comprise corresponding instructions to the laboratory operator. These instructions may comprise one or more of at least one request, at least one managing or controlling information, at least one handling information, and at least one teaching information. For example, the augmented reality device may for instance support the laboratory operator when servicing at an instrument. With the corresponding event published on the data server, a notification for the laboratory operator may be derived. The augmented reality device may then, for instance, show instructions for guidance or materials needed next to the instrument, when the laboratory operator looks at it. In a service mode, the augmented reality device may show further details such as safety remarks, a simulation of the service activities or an assisted service video on command. The term "command" as used herein can be a broad term and can be given its ordinary and customary meaning to a person of ordinary skill in the art and may not be limited to a special or customized meaning. The term specifically may refer, without limitation, to gestures and/or verbal expressions and/or key presses or the like conducted by the laboratory operator. The term "on command" as used herein can be a broad term and can be given its ordinary and customary meaning to a person of ordinary skill in the art and may not be limited to a special or customized meaning. The term specifically may refer, without limitation, to commands, which can be registered by the augmented reality device as orders for corresponding follow-up actions such as specifically displaying new information and/or instructions. The laboratory operator may also be given the opportunity to select from a set of different information and/or instructions in such situations.

The augmented reality device may be configured in a way that the laboratory operator can select from different interaction opportunities such as a user menu, possessions, or a task list depending on the present location. Carrying out a chosen action an instrument may then for instance wake up, calibrate, open a drawer and locate a sample, or, in case of an IT solution, inventories and status may be updated.

Guidance may also specifically be given to exchange spare parts. It may be displayed by the augmented reality device as described above, the ID of the part to be replaced and the spare part may be captured as well as a confirmation of its proper placement. The information may be stored on the data server for documentation. No further support may be necessary during the entire process, so that a notable reduction of Field Service Engineers (FSE) can be reached.

The augmented reality information may be used for one or more of: teaching the laboratory operator, changing a status of the laboratory resource such as updating an instrument or repairing the instrument, invalidating or validating a sample tube or reagent cassette. The augmented reality information may be considered when conducting a test using the laboratory resource, tracking of the different states, troubleshooting purposes, influencing the overall systems workflows, performing system maintenance, performing teaching and diagnostics services.

For example, the augmented reality information may be used to effect a change in the laboratory resource. For instance, a reagent cassette may be invalidated for multiple reasons and as a consequence potentially also discarded. Certain tests may be performed with the laboratory resource following the information and/or instructions given by the augmented reality device. By this, the laboratory resource may also undergo a modification, such as, for instance, a volume change in the compartments of a reagent cassette. Specifically, in regard to instruments as laboratory resources, servicing and teaching guided via augmented reality information may have direct impact on not only the laboratory resource, but also the laboratory operator. The modification on the instrument may be an exchanged part or updated software. The impact on the laboratory operator may refer to the corresponding gain in technical knowledge.

In a further aspect of the present invention, a tracking system is disclosed. The tracking system can comprise at least one data server and at least one augmented reality device. The augmented reality device can comprise at least one imaging sensor configured for detecting the laboratory resource in the laboratory. The augmented reality device can comprise at least one identification unit configured for identifying the laboratory resource by receiving at least one identification information from the identification feature. The augmented reality device can comprise at least one communication interface. The communication interface can be configured for retrieving information about the identified laboratory resource from the data server. The augmented reality device can comprise at least one display device. The augmented reality device can be configured for generating and displaying at least one augmented reality information on the display device. The augmented reality information can comprise at least one hologram comprising the retrieved information about the identified laboratory resource and/or at least one instruction depending on the retrieved information about the identified laboratory resource.

Specifically, the analytical system may be configured for performing the method according to the present disclosure and/or for being used in the method according to the present disclosure. For definitions of the features of the tracking system and for optional features of the tracking system, reference may be made to one or more of the embodiments of the method as disclosed above or as disclosed in further detail below.

The term "system" as used herein can be a broad term and can be given its ordinary and customary meaning to a person of ordinary skill in the art and may not be limited to a special or customized meaning. The term specifically may refer, without limitation, to an arbitrary set of interacting or interdependent components parts forming a whole. Specifically, the components may interact with each other in order to fulfill at least one common function. The at least two components may be handled independently or may be coupled or connectable. The term "tracking system" as used herein can be a broad term and can be given its ordinary and customary meaning to a person of ordinary skill in the art and may not be limited to a special or customized meaning. The term specifically may refer, without limitation, to a group of at least two elements or components, which can be capable of interacting in order to perform at least one tracking process of at least one laboratory resource in a laboratory. The tracking process may comprise method steps a)-c) according to the present disclosure.

In a further aspect of the present disclosure, a computer program is disclosed. The computer program can comprise instructions which, when the program is executed by the tracking system according to the present disclosure, such as according to any one of the embodiments disclosed above and/or according to any one of the embodiments disclosed in further detail below, can cause the tracking system to carry out at least step a) to c) of the method according to the present disclosure, such as according to any one of the embodiments disclosed above and/or according to any one of the embodiments disclosed in further detail below.

The method may comprise steps, which can be partially computer-implemented and required, in addition to user action. For the steps, which may not be computer-implemented or computer-implementable, the computer program may imply a prompting of the user to perform specific acts. Thus, as an example, the computer program may comprise instructions which, when executed, prompt the user to look at a laboratory resource, such as for performing step a) of the method. The prompting, as an example, may take place by visually displaying instructions, e.g., on a display of the augmented reality device, and/or by other means, such as by providing audible instructions. Step b) may be fully computer-implemented by the computer program, in particular as long as the augmented reality device is connected to the data server. If the augmented reality device is not connected to the data server, the laboratory operator may be asked for connection. If the laboratory resource is not known, the data server may return and display "nothing" in step b) and step c). In the case the data server returns that the laboratory resource is not known, the augmented reality device may prompt the laboratory operator to update the database of the data server and/or to repeat step a). The computer program may comprise instructions, which, when the program is executed by the tracking system according to the present disclosure, can cause the tracking system to prompt the user to initiate step a), to optionally prompt the user to assist in performing step b) if necessary and, further, to optionally carry out step c) automatically.

Disclosed and proposed herein is a modulated data signal, which can contain instructions readable by a computer system or computer network, for performing the method according to one or more of the embodiments disclosed herein.

Similarly, a computer-readable storage medium is disclosed comprising instructions which, when executed by the tracking system according to the present disclosure, such as according to any one of the embodiments disclosed above and/or according to any one of the embodiments disclosed in further detail below, can cause the analytical system to carry out at least step a) to c) of the method according to the present disclosure, such as according to any one of the embodiments disclosed above and/or according to any one of the embodiments disclosed in further detail below. For the options of prompting the user to assist in some of the method steps, specifically in steps a) and b), reference can be made to the description of the computer program.

The term "computer-readable storage medium" as used herein can be a broad term and can be given its ordinary and customary meaning to a person of ordinary skill in the art and may not be limited to a special or customized meaning. The term specifically may refer, without limitation, to a non-transitory data storage such as, for example, a hardware storage medium having stored there-on computer-executable instructions. The computer-readable data carrier or storage medium specifically may be or may comprise a storage medium such as a random-access memory (RAM) and/or a read-only memory (ROM).

The computer program may also be embodied as a computer program product. As used herein, a computer program product may refer to the program as a tradable product. The product may generally exist in an arbitrary format, such as in a paper format, or on a computer-readable data carrier and/or on a computer-readable storage medium. Specifically, the computer program product may be distributed over a data network.

The proposed method and system can provide a large number of advantages over known methods and devices of similar kind. Using the augmented reality device capable of identifying laboratory resources by different features laboratory operators do not need to touch the potentially harmful laboratory resources anymore during identification process. Without interruption, they can carry on their workflows. This can especially include the kind requiring them to wear safety gloves and use both hands in a laboratory environment. Since information and instructions for the laboratory resource of interest can be directly displayed by the augmented reality device, a transport to a corresponding instrument capable of analyzing the laboratory resource can become redundant. Considering, specifically, such an instrument itself as laboratory resource, the use of an augmented reality device as a tutor further can lead to a reduction of FSE presence for small upgrades in the equipment. Overall, the described method and devices therefore do not only allow for a safer, but also for a faster access to information and instructions irrespective of the position of the laboratory operator, because by this method, a previously device centered access changes to a user centered access. In this manner, the described method can lead to safer and more efficient workflows in a laboratory environment.

A computer-implemented method for tracking of at least one laboratory resource in a laboratory is disclosed. The laboratory resource can comprise at least one identification feature. The method can comprises a) at least one identification step comprising detecting the laboratory resource in the laboratory with at least one imaging sensor of at least one augmented reality device and identifying the laboratory resource with at least one identification unit of the augmented reality device by receiving at least one identification information from the identification feature; b) at least one data retrieving step comprising retrieving information about the identified laboratory resource from at least one data server via at least one communication interface of the augmented reality device; and c) at least one tracking step comprising generating and displaying at least one augmented reality information on at least one display device of the augmented reality device. The augmented reality information can comprise at least one hologram comprising the retrieved information about the identified laboratory resource and/or at least one instruction depending on the retrieved information about the identified laboratory resource.

The steps a) to c) can be performed fully automatically.

The laboratory resources can comprise at least one element selected from the group comprising of: at least one sample tube; at least one reagent cassette; at least one processing plate; at least one instrument and/or at least one internal control.

The laboratory resource can comprise the sample tube. The hologram can comprise one or more of a barcode, a sample type, a tube type, information about a test result, and information about a test such as, for example, a test protocol.

The laboratory resource can comprise the reagent cassette. The hologram can comprise one or more of a lot number, a barcode, expiration date, storage information, validity information, and status information.

The laboratory resource can comprise at least one instrument. The hologram can comprise one or more of status information, processing information, maintenance information, software version, and usage information.

The instruction can comprise instructions for a laboratory operator of the laboratory and/or instructions for at least one device of the laboratory. The instructions can comprise one or more of at least one request, at least one managing or controlling information, at least one handling information, and at least one teaching information.

The identification feature can comprise one or more of at least one barcode, at least one QR code, at least one radio frequency identification tag, and/or at least one near field communication tag.

Step a) can comprise scanning the identification tag.

Step a) can comprise imaging the laboratory resource with the imaging sensor and evaluating at least one image of the laboratory resource using at least one processor of the augmented reality device.

The data server can comprise one or more of at least one computer, at least one computer network, and/or at least one cloud server.

The method can comprise at least one data-publishing step comprising at least one Laboratory Information System (LIS) and/or middleware and/or instrument of the laboratory publishing data about the laboratory resource and/or the laboratory and/or the instrument on the data server.

In step b), the communication interface can transmit at least one request to the data server asking for the information about the identified laboratory resource with the identification information. The request can be a HTTP- or AMQP-based request.

The method can comprise the augmented reality device associating the hologram and the laboratory resource such that the hologram can be displayed next to the laboratory resource on the display device.

The augmented reality device can be at least one portable and/or wearable augmented reality device. The method can further comprise positioning the augmented reality device in the laboratory at a position of interest.

A tracking system for tracking of at least one laboratory resource in a laboratory is disclosed. The laboratory resource can comprise at least one identification feature. The tracking system can comprise at least one data server and at least one augmented reality device. The augmented reality device can comprise at least one imaging sensor configured for detecting the laboratory resource in the laboratory. The augmented reality device can comprise at least one identification unit configured for identifying the laboratory resource by receiving at least one identification information from the identification feature. The augmented reality device can comprise at least one communication interface. The communication interface can be configured for retrieving information about the identified laboratory resource from the data server. The augmented reality device can comprise at least one display device. The augmented reality device can be configured for generating and displaying at least one augmented reality information on the display device. The augmented reality information can comprise at least one hologram comprising the retrieved information about the identified laboratory resource and/or at least one instruction depending on the retrieved information about the identified laboratory resource.

The tracking system can be configured for performing the method according to any one of the preceding embodiments.

A computer program comprising instructions which, when executed by the tracking system according to any one of the preceding embodiments referring to a tracking system, can cause the tracking system to carry out at least step a) to c) of the method according to any one of the preceding embodiments.

A computer-readable storage medium comprising instructions which, when executed by the tracking system according to any one of the preceding embodiments referring to a tracking system, can cause the tracking system to carry out at least step a) to c) of the method according to any one of the preceding embodiments.

Referring initially to FIG. 1, FIG. 1 shows an embodiment of a tracking system 110 and a method for tracking at least one laboratory resource 112 according to the present disclosure used for tracking a sample tube 114 in a laboratory. The laboratory may be a location configured for work in the field of the natural sciences and/or engineering in the sense that it can offer the opportunity to conduct corresponding measurements and controls.

The laboratory resource 112 may comprise at least one element selected from the group comprising of: at least one sample tube; at least one reagent cassette; at least one processing plate; at least one instrument; at least one internal control and the like. In the example of FIG. 1, the laboratory resource 112 of interest may be the sample tube 114.

The laboratory resource 112 can comprise at least one identification feature 116. The identification feature 116 may be or comprise any aspect, character or detail of the laboratory resource 112. The identification feature 116 may, for example, be or may comprise one or more of shape, color or identification tags placed on it. The identification feature 116 may be configured for visually distinguishing the laboratory resource from other laboratory resources. The identification feature 116 may comprise at least one element or a combination of elements configured for storing one or more items of information identifying the laboratory resource, such as in a readable fashion, specifically in a machine-readable fashion. The identification feature 116 may comprise at least one of an optical identification feature, an electronic identification feature, a magnetic identification feature or a mechanical identification feature. The identification feature 116 may comprise at least one marker. As an example, the identification feature, specifically the optical identification feature, may be or may comprise at least one of a one- or two-dimensional code and/or a readable information tag, such as one or more of a barcode, a QR code or another type of code directly or indirectly attached to the laboratory resource, such as by being applied directly to the laboratory resource and/or by being attached to the laboratory resource via at least one label or tag. The information stored in the identification feature 116 may be read using an appropriate reading device. The identification feature may comprise one or more of at least one barcode, at least one QR code, at least one radio frequency identification tag, and at least one near field communication tag.

The identification feature 116 may comprise identification information. As an example, the identification information specifically may comprise at least one identification number of the laboratory resource 112. The identification information may comprise one or more of shape, color, barcode, RFID tag, or other tagging systems. The identification number may be unique for a specific laboratory resource 112. Thus, it may be possible to identify a specific laboratory resource 112 according to the respective identification number.

For example, the sample tube 114 may comprise at least one barcode. The barcode may comprise binary optical information, such as to a binary sequence of optical information, such as a sequence of parallel lines having different widths, the binary sequence encoding information such as a number and/or an array of numbers and/or letters. Thus, the barcode may be a sequence of single colored lines having a high contrast compared to a background. Specifically, the barcode may comprise black lines on a white background.

In the embodiment shown in FIG. 1, the sample tube 114 may be received by an instrument 118 such as, for example, a pre-analytical instrument. After processing the sample 114 on the instrument 118, a laboratory operator 120 may be required to first check out a result of the processing and what is a next instrument that may need to receive the sample tube, given the case of a non-automated laboratory. With known methods, the laboratory operator 120, firstly, would need check on the pre-analytical instrument, which processed the sample or the LIS what was the result of the processing and, secondly, would need to check on the LIS or middleware which instrument may need to receive the processed sample tube 114. Such known methods can be time consuming and complex. The method and tracking system 110 of the present disclosure can have the advantage of allowing simplified and, for the laboratory operator 120, comfortable identification of laboratory resources 112.

The tracking system 110 can comprise at least one augmented reality device 122. The augmented reality device 122 may be configured for augmenting an image of a physical object with computer-based additional information. The additional information may be denoted as augmented reality information 124 in the following. The augmented reality information 124 may comprise, for example, visual and/or auditory information. The augmented reality information 124 may be at least one virtual object from a data server by picture-in-picture fade-in. The augmented reality information 124 may be constructive such as an additive or may be destructive such as by masking. The augmented reality device 122 may comprise one or more of at least one processing device 126, at least one display device 150, at least one sensor 128, such as the at least one imaging sensor 130, at least one accelerometer, at least one gyroscope and the like, and at least one input device. The augmented reality device 122 may comprise an optical projection system configured for projecting augmented reality information 124 to a laboratory operator 120.

The augmented reality device 122 may be at least one portable and/or wearable augmented reality device. The augmented reality device 122 as a whole may further be portable and/or wearable, so that it may easily be positioned in the laboratory at a position of interest. The augmented reality device 122 may be worn by the user such as by a laboratory operator 120. The augmented reality device 122 may comprise eyeglasses. For example, the augmented reality device 122 may be designed as Microsoft HOLOLENS™ device.

The augmented reality device 122 can comprise at least one imaging sensor 130 configured for detecting the laboratory resource 112 in the laboratory. As an example, the imaging sensor 130 may comprise at least one camera chip, such as at least one CCD chip and/or at least one CMOS chip configured for recording images. The imaging sensor 130 may be configured for generating and/or recording at least one image of the laboratory resource 112 and/or at least one part of the laboratory resource 112, such as of the identification feature 116. The imaging sensor 130 may be integrated in the augmented reality device 122. The detecting of the laboratory resource 112 may comprise imaging the laboratory resource 112 and/or at least sectors or parts of the laboratory resource 112. Specifically, the detecting of the laboratory resource 112 may comprise detection of at least one physical object such as of the sample tube 114 on the physical world.

In the embodiment of FIG. 1, the laboratory operator 120 wearing the augmented reality device 122 may directly look at the sample tube 114, shown with reference number 132. The augmented reality device 122 may try to find which kind of element the user is looking at by detecting the identification feature 116. The method may comprise imaging the laboratory resource 112 with the imaging sensor 130 and evaluating at least one image of the laboratory resource 112 using at least one processing device 126 of the augmented reality device 122. Thus, as an example, the augmented reality device 122 may comprise one or more programmable devices such as one or more computers, microprocessors, application-specific integrated circuits (ASICs), Digital Signal Processors (DSPs), or Field Programmable Gate Arrays (FPGAs), which can be configured to perform the evaluation. The evaluation may comprise using at least one image-processing algorithm.

Once the type of element is detected, the augmented reality device 122 may start scanning the barcode on the sample tube 114, denoted with reference number 134. The scanning may comprise retrieving at least one item of information such as, for example, the at least one item of information stored in the identification information such as, for example, in an electronic format. The reading specifically may take place electronically. The process of scanning may depend on the type of identification information. Thus, the scanning may comprise an optical reading in the case the identification information comprises an optical identification information, such as a bar code and/or a QR code, e.g., by optical scanning. In the case the identification information comprises an electronic identification information, such as an RFID code, the reading may comprise an electronic reading, such as a reading by near field communication (NFC). Other options can be feasible.

The augmented reality device 122 can comprise the at least one identification unit 136. The identification unit 136 may comprise at least one reading device. The reading device may be configured to perform the scanning process as defined above, such as to a device configured to read the identification information stored by the identification feature 116. Specifically, the reading device may be or may comprise at least one of: a one- or two-dimensional scanner, a camera and/or a radio frequency reading device, such as a NFC reader. The reading device may be integrated into the augmented reality device 122. Additionally, or alternatively, the reading device may be designed as separate element. The reading device may further be configured to communicate with the identification unit 136. Specifically, the reading device may be configured to transfer the identification information to the identification unit 136 such as, for example, to a processor of the identification unit 136.

The augmented reality device 122 can comprise at least one communication interface 138. The communication interface 138 may be configured for transferring information from a computational device, e.g., a computer, such as to send or output information, e.g., onto another device. Additionally, or alternatively, the communication interface 138 may be configured for transferring information onto a computational device, e.g., onto a computer, such as to receive information. The communication interface 138 may specifically provide transferring or exchanging information. In particular, the communication interface 138 may provide a data transfer connection, e.g., Bluetooth, NFC, inductive coupling or the like. As an example, the communication interface 138 may be or may comprise at least one port comprising one or more of a network or internet port, a USB-port and a disk drive. The communication interface 138 may be at least one web interface.

The tracking system 110 can comprise at least one data server 140. The communication interface 138 can be configured for retrieving information about the identified laboratory resource 112 from the data server 140. The communication interface 138 may transmit at least one request to the data server 140 asking for the information about the identified laboratory resource 112 with the identification information, denoted with reference number 139. The request may be a HTTP-based request and/or an AMQP-based request.

The data server 140 may comprise one or more of at least one computer, at least one computer network, at least one cloud server. The data server 140 may be deployed both locally, e.g., on premises, or in the cloud. The data server 140 may comprise at least one database. The database may comprise or may be comprised by a data storage device. The database may comprise at least one data base management system, comprising a software running on a computer or computer system, the software allowing for interaction with one or more or a user, an application or the database itself, such as in order to capture and analyze the data contained in the database. The database management system may further encompass facilities to administer the database. The database, containing the data, may, thus, be comprised by a data base system, which, besides the data, can comprise one or more associated applications.

The data server 140 may be configured for subscribing to some events generated by at least one laboratory instrument such as the instrument 118. The method may comprise at least one data-publishing step, denoted with reference number 142. The data server 140 may provide an instance of a Message bus where instruments of the laboratory and also Laboratory Information System (LIS) 144 and/or middleware 146 can publish information in the shape of events. The data-publishing step 142 may comprise at least one LIS 144 and/or middleware 146 and/or instrument of the laboratory publishing data about the laboratory resource 112 and/or the laboratory and/or the instrument on the data server 140. The LIS and/or middleware may publish data about workflows and/or a sample status. An instrument may publish data on its status and/or the resource usage and/or the resource loading. The data server 140 may subscribe to those events and use them to project data into the database, such as to a document database, which will be used to return the data to the augmented reality device 122 when it queries for data. The data server 140 may be configured for generating and storing projected data out of the received events in the database. Specifically, the data-publishing step 142 may comprise confirming a search request for the laboratory resource 112 of interest filed on the data server 140 together with follow-up actions.

The event may comprise a human-machine interaction such as a key press and/or sensor output such as a certain visual signal and/or software commands from other programs. These events may cause a program to execute specific corresponding routines instead of linearly running through the underlying program code.

The data server 140 may be configured for providing an instance, where instruments and/or the LIS 144 and/or middleware 146 may be given the opportunity to publish information in the shape of events. For this purpose, the message bus may be used. The data server 140 may comprise at least one interface for data access, in particular, at least one HTTP-based interface. Specifically, the data server 140 may provide a RESTFul API, which may enable the augmented reality device to query for data. The RESTful API refers to an Application Programming Interface (API) for the Representational State Transfer (REST) programming paradigm mainly used for web services.

In the example show in FIG. 1, in response to the request from the augmented reality device 122 the data server 140 may return, see reference number 148, information about the sample tube 114 or "nothing" if the sample tube 114 is not known.

The augmented reality device 122 can comprise at least one display device 150. The display device 150 may comprise at least one projector and/or at least one screen. The augmented reality device 122 may comprise at least one head-mounted display (HMD). The display device 150 may be configured for imaging of both the physical world, the real laboratory resource, and virtual objects over the user's field of view.

The augmented reality device 122 can be configured for generating and displaying the at least one augmented reality information 124 on the display device 150. The augmented reality information 124 can comprise the at least one hologram 152 comprising the retrieved information about the identified laboratory resource 112 and/or at least one instruction depending on the retrieved information about the identified laboratory resource 112. The augmented reality information 124 may comprise, for example, visual and/or auditory information. The augmented reality information 124 may be at least one virtual object from a database. The augmented reality information 124 may be constructive such as an additive or may be destructive such as by masking. The augmented reality information 124 may be or may comprise at least one augmented reality representation of different states of the laboratory resources 112. The augmented reality information may be or may comprise digital information.

With the received data from the data server 140, the augmented reality device 122 may render the hologram 152 next to the physical object showing the received information. The information about the identified laboratory resource, as outlined above, may be retrieved by the augmented reality device from the data server and may be displayed to the laboratory operator by the display device of the augmented reality device, e.g., via picture-in-picture fade-in. The hologram 152 may comprise at least one object selected from the group consisting of: a barcode, sample type, tube type, last available result, last performed test or protocol, next target instrument, next test to be performed, expiration date, storage information, validity information, status information, processing information, maintenance information, software version, usage information, at least one request, at least one managing or controlling information, at least one handling information, and at least one teaching information. For example, for the embodiment of FIG. 1, the hologram 152 may comprise one or more of a barcode, sample type, tube type, last available result, last performed test or protocol, next target instrument, next test to be performed. Repeating the operation may be possible at any time by looking at the sample tube 114 again.

Figure 2:
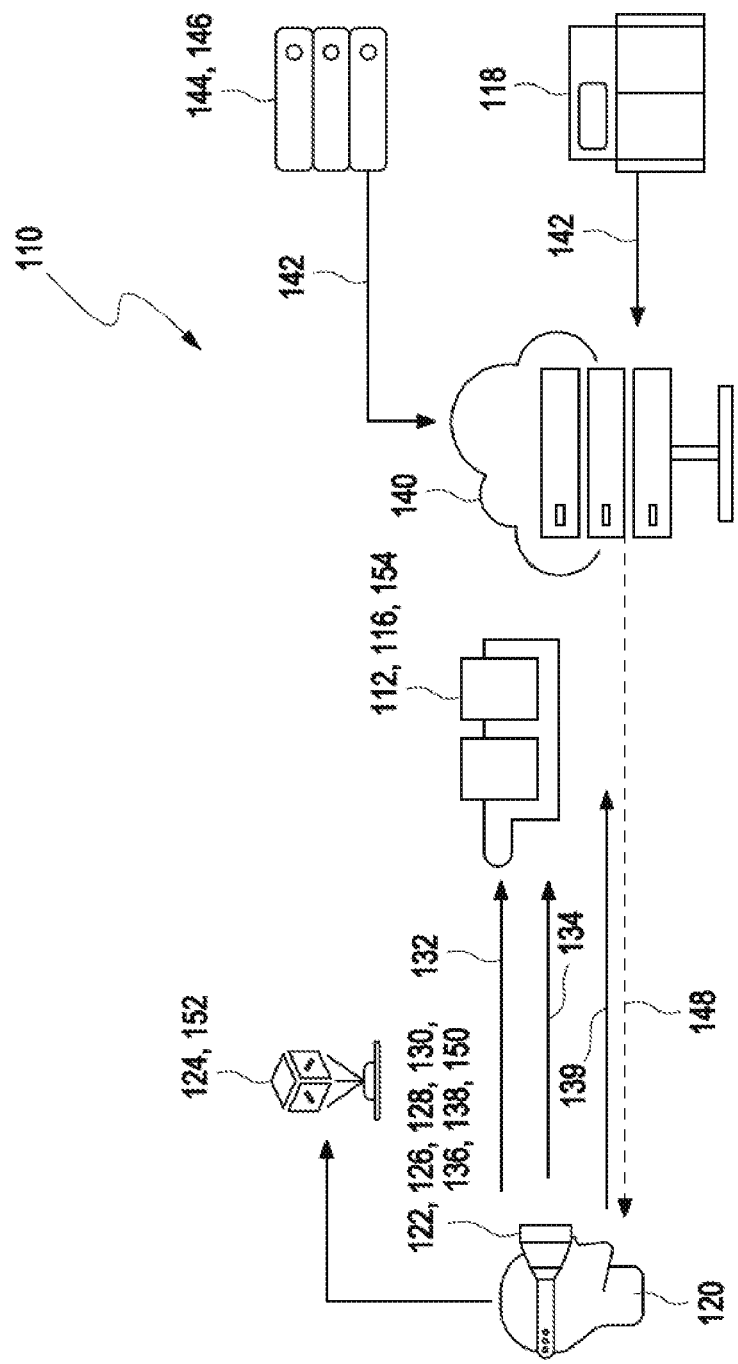
FIG. 2 illustrates tracking a reagent cassette in a laboratory using the tracking system and the method according to an embodiment of the present disclosure.

FIG. 2 shows tracking of a reagent cassette 154 in a laboratory using the tracking system 110 and the method according to the present disclosure. Reagent cassettes 154 may be always stored in a refrigerator and can only stay out of the refrigerator a certain amount of time without changing properties. Thus, tracking the time they were not refrigerated can be of special importance. In addition, an instrument can invalidate a reagent cassette 154 because of multiple reasons. The laboratory operator 120 may need to know if a reagent cassette 154 is still valid or not before loading it into an instrument. Finally, a reagent cassette 154 may be made of one or more compartments, which can contain different liquids. Some instruments might use all the compartments or only a few of them. It may be important for the operator to know how much volume is left on each compartment in order to use or not this reagent cassette 154 for a concrete test.

As for the case of the sample tube 114 in FIG. 1, the provided method and devices support the laboratory operator 120 also for the case of reagent cassettes 154 here, as depicted in FIG. 2. As described with respect to FIG. 1, instruments as well as the LIS 144 or middleware 146 can publish data on a data server 140 in at least one data publishing step 142.

It can be noted at this point, that the mentioned elements and steps here and in the following lines may be identical to those elements and steps in FIG. 1, but may also be different in aspects of subordinated importance to the principles of the provided method. The instrument may for instance be a different one fulfilling different tasks in the laboratory and thus publish different data on as an example its status. Nevertheless, to the provided method, it still can remain in the role of an instrument and the approach of the provided method is not affected by this kind of modification.

In the embodiment of FIG. 2, the laboratory operator 120 wearing the augmented reality device 122 may directly look at the reagent cassette 154 of interest, shown with reference number 132. The augmented reality device 122 then may try to find out which type of laboratory resource 112 the laboratory operator 120 is looking at by detecting the identification feature 116. Once the type, in this case the reagent cassette 154, is detected, the augmented reality device 122 may start scanning for a barcode, denoted with reference number 134. Once the barcode is read, the augmented reality device 122 may transmit at least one request to the data server 140 asking for the information about the identified laboratory resource 112 with the identification information, denoted with reference number 139. In the example show in FIG. 2, in response to the request from the augmented reality device 122, the data server 140 may return, see reference number 148, information about the reagent cassette 154 or "nothing" if the reagent cassette 154 is not known. The augmented reality device 122 may render the hologram 152 next to the reagent cassette 154 displaying the augmented reality information 124 on the display device 150. The augmented reality information 124 may comprise one or more of: a lot number, the barcode, expiration date, on board time inside an instrument, remaining ticks such as usages, or left volume on each compartment of the reagent cassette 154, information on how long the reagent cassette 154 has been out of a refrigerator, or whether it is still valid or invalid may be options in this situation. Repeating the operation may be possible at any time by looking at the reagent cassette 154 again.

Figure 3:
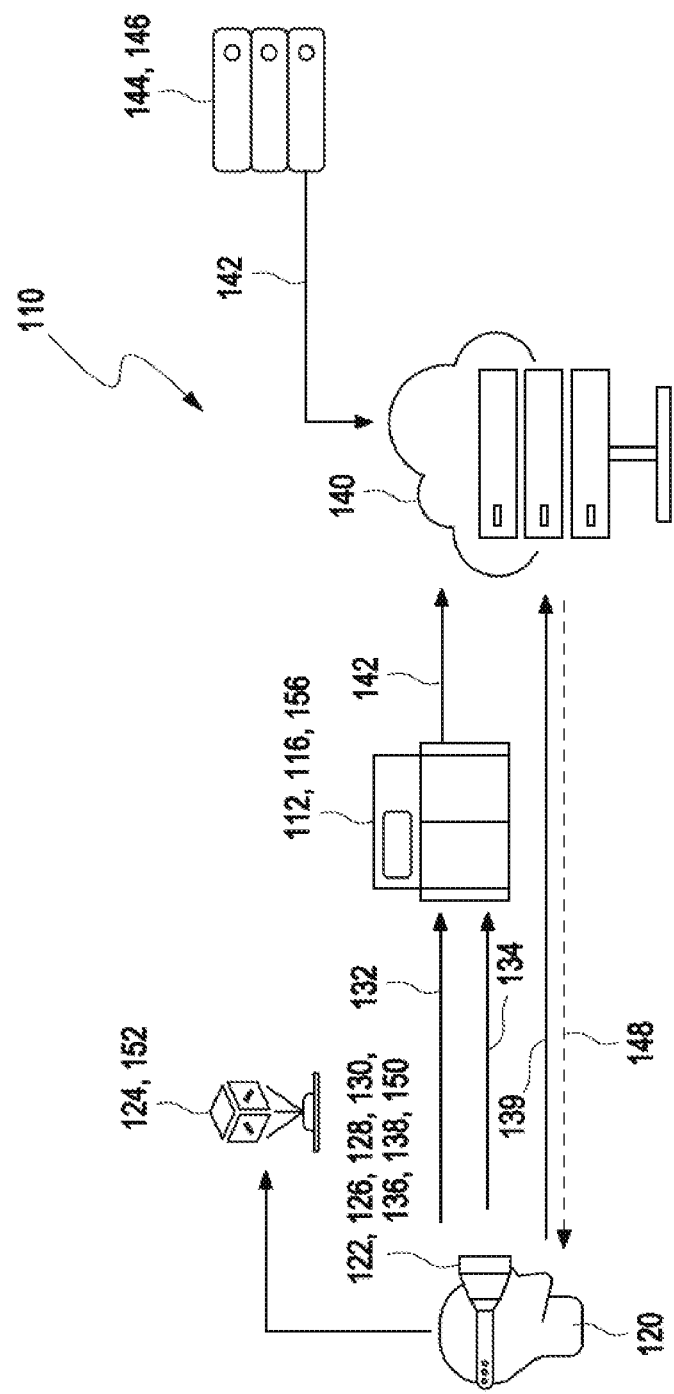
FIG. 3 illustrates tracking a state of an instrument in a laboratory using the tracking system and the method according to an embodiment of the present disclosure.

FIG. 3 shows tracking a state of an instrument 156 in a laboratory using the tracking system 110 and the method according to the present disclosure. Not every instrument in the field may have a display. Some of them may be operated through an application deployed on a separate personal computer (PC) or laptop. This may require the laboratory operator 120 to move to another location in order to interact with the instrument or to only check what the instrument is doing. The tracking system 110 and the method according to the present disclosure can solve this issue by rendering a hologram 152, which can show the current state of the instrument next to it.

In the embodiment of FIG. 3, the laboratory operator 120 wearing the augmented reality device 122 may directly look at the instrument 156 of interest, shown with reference number 132. The augmented reality device 122 then may try to find out which type of laboratory resource 112 the laboratory operator 120 is looking at by detecting the identification feature 116. In the case of instruments 156, a marker may be used to identify which kind of instrument the operator is looking at. Once the type, in this case the instrument 156, is detected, the augmented reality device 122 may start scanning for a barcode, denoted with reference number 134. Once the barcode is read, the augmented reality device 122 may transmit at least one request to the data server 140 asking for the information about the identified laboratory resource 112 with the identification information, denoted with reference number 139. In the example shown in FIG. 3, in response to the request from the augmented reality device 122, the data server 140 may return, see reference number 148, information about the instrument 156 or "nothing" if the reagent cassette 154 is not known. The augmented reality device 122 may render the hologram 152 next to the reagent cassette 154 displaying the augmented reality information 124 on the display device 150. The augmented reality information 124 may comprise one or more of: instrument status, currently processing test, batch or order ID, the next maintenance, loaded resource status, such as how much volume is left on loaded reagent cassettes or how many tips are left in a tip rack, the software version, the last teaching, the allowed tests to be run on the instrument 156. schedule of runs, previous results, ordering information, state of loaded samples in the instrument, state of loaded resources in the instrument, status of executing runs, list of pending runs, estimated times till next result and next run start. Repeating the operation may be possible at any time by looking at the instrument 156 again.

Figure 4:
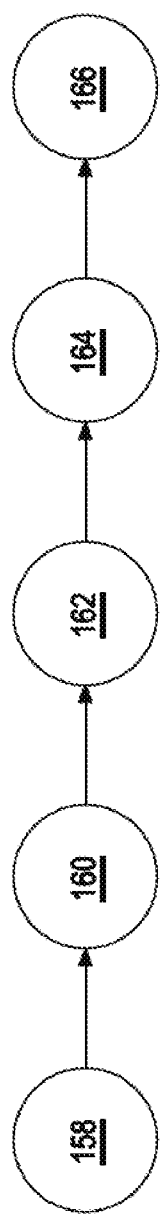
FIG. 4 illustrates a flow chart of the method according to an embodiment of the present disclosure.

FIG. 4 shows a flow chart of an embodiment of the method according to the present invention. Specifically, FIG. 4 illustrates the high level of reaction to events based on the tracking system 110. This embodiment can refer to servicing at an instrument. In the case an event is published, denoted with reference number 158, a notification 160 may be directly displayed to the laboratory operator 120 via the augmented reality device 122 offering guidance and/or listing required materials. In step 162, information about location may be provided for the event to the operator. An event can reflect a fact that occurred in the system. It is a past-tense formulation of a fact that can be later used for behavioral analysis of the system. The location may be a physical geolocation of the laboratory resource. The augmented reality device 122 may switch to a service mode 164 and can be operated on command. Service mode details 166 may comprise guidance and confirmation, as well as a simulation of service activity, safety activity such as marking contaminated area and checking the position of the laboratory operator, an assisted service, at least one video.

Figure 5:
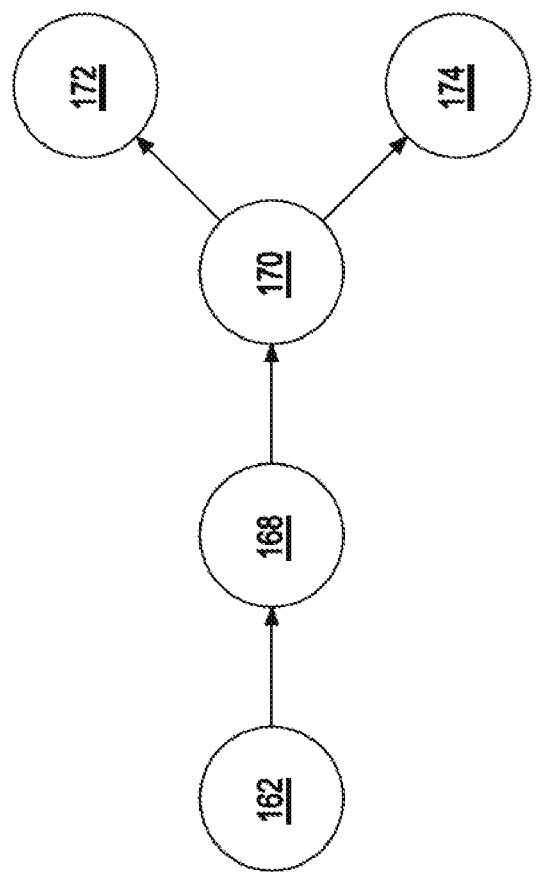
FIG. 5 illustrates a flow chart for possible tasks of a laboratory operator in a laboratory in connection with an instrument according to an embodiment of the present disclosure.

FIG. 5 shows a flow chart for possible tasks of a laboratory operator in a laboratory in connection with an instrument. Specifically, FIG. 5 shows high-level view of reaction to events based on the tracking system 110. FIG. 5 focusses on possible tasks of the laboratory operator 120 for an instrument. In step 162, information about location may be provided for the event to the operator. The hologram 152 may comprise a selection of actions 168 comprising one or more of a task list, possessions and a user menu. The possessions may be physical or virtual objects that might be needed so that the laboratory operator or a customer can perform a task. The laboratory operator 120 may execute, denoted as reference number 170, and carry out actions. For example, denoted with reference number 172, the actions may comprise one or more of wake up the instrument, calibrate, open a drawer and locate a sample. Alternatively, denoted with reference number 174, the laboratory operator 120 may carry out an IT solution such as inventories and status updates.

Additionally, or alternatively, the hologram 152 may comprise guidance to exchange spare parts. For example, a guidance may be displayed, an ID of a part may be captured, and an ID of a spare part and confirmation of proper placement may be captured and stored for documentation. This scenario may reduce need of FSE at the laboratory.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A computer implemented method for tracking of at least one laboratory resource in a laboratory, wherein the laboratory resource comprises at least one identification feature, the method comprises:
   a) at least one identification step, wherein the identification step comprises detecting the laboratory resource in the laboratory with at least one imaging sensor of at least one augmented reality device and identifying the laboratory resource with at least one identification unit of the augmented reality device by receiving at least one identification information from the identification feature;
   b) at least one data retrieving step, wherein the data retrieving step comprises retrieving information about the identified laboratory resource from at least one data server via at least one communication interface of the augmented reality device;
   c) at least one tracking step, wherein the tracking step comprises generating and displaying at least one augmented reality information on at least one display device of the augmented reality device, wherein the augmented reality information comprises at least one hologram comprising the retrieved information about the identified laboratory resource and/or at least one instruction depending on the retrieved information about the identified laboratory resource; and
   d) at least one data publishing step, wherein the data publishing step comprises at least one Laboratory Information System (LIS) and/or middleware and/or instrument of the laboratory publishing data about the laboratory resource and/or the laboratory and/or the instrument on the data server;
wherein the laboratory resource comprises:
   a processing plate wherein the hologram comprises one or more of a barcode, batch or order ID, or information about a test such as a test protocol.

2. The method according to claim 1, wherein steps a) to c) are performed fully automatically.

3. The method according to claim 1, wherein the laboratory resources comprise at least one element selected from the group comprising: at least one instrument, and/or at least one internal control.

4. The method according to claim 1, wherein the laboratory resource comprises the sample tube, wherein the hologram comprises one or more of a barcode, a sample type, a tube type, information about a test result, and information about a test such as a test protocol.

5. The method according to claim 1, wherein the laboratory resource comprises the reagent cassette, wherein the hologram comprises one or more of a lot number, a barcode, expiration date, storage information, validity information, and status information.

6. The method according to claim 1, wherein the laboratory resource comprises at least one instrument, wherein the hologram comprises one or more of status information, processing information, maintenance information, software version, and usage information.

7. The method according to claim 1, wherein the instruction comprises instructions for a laboratory operator of the laboratory and/or instructions for at least one device of the laboratory, wherein the instructions comprise one or more of at least one request, at least one managing or controlling information, at least one handling information, and at least one teaching information.

8. The method according to claim 1, wherein the identification feature comprises one or more of at least one barcode, at least one QR code, at least one radio frequency identification tag, and at least one near field communication tag.

9. The method according to claim 1, wherein step a) comprises scanning the identification feature.

10. The method according to claim 1, wherein step a) comprises imaging the laboratory resource with the imaging sensor and evaluating at least one image of the laboratory resource using at least one processor of the augmented reality device.

11. The method according to claim 1, wherein the at least one data server comprises one or more of at least one computer, at least one computer network, and/or at least one cloud server.

12. The method according to claim 1, wherein in step b), the communication interface transmits at least one request to the at least one data server asking for the information about the identified laboratory resource with the identification information.

13. The method according to claim 12, wherein the request is a HTTP-based request and/or an AMQP-based request.

14. The method according to claim 1, further comprises, associating the hologram and the laboratory resource by the augmented reality device such that the hologram is displayed next to the laboratory resource on the display device.

15. The method according to claim 1, wherein the augmented reality device is at least one portable and/or wearable augmented reality device, wherein the method comprises positioning the augmented reality device in the laboratory at a position of interest.

16. A tracking system for tracking of at least one laboratory resource in a laboratory, wherein the laboratory resource comprises at least one identification feature, the tracking system comprising:
   at least one data server; and
   at least one augmented reality device, wherein the augmented reality device comprises at least one imaging sensor configured for detecting the laboratory resource in the laboratory, wherein the augmented reality device comprises at least one identification unit configured for identifying the laboratory resource by receiving at least one identification information from the identification feature, wherein the augmented reality device comprises at least one communication interface, wherein the communication interface is configured for retrieving information about the identified laboratory resource from the data server, wherein the augmented reality device comprises at least one display device, wherein the augmented reality device is configured for generating and displaying at least one augmented reality information on the display device, wherein the augmented reality information comprises at least one hologram comprising the retrieved information about the identified laboratory resource and/or at least one instruction depending on the retrieved information about the identified laboratory resource;
wherein the laboratory resource comprises:
   a processing plate wherein the hologram comprises one or more of a barcode, batch or order ID, or information about a test such as a test protocol.

* * * * *